United States Patent [19]
Levy

[11] Patent Number: 5,147,042
[45] Date of Patent: Sep. 15, 1992

[54] HOLDER FOR MEDICAL SPECIMEN SLIDE

[76] Inventor: Abner Levy, 325 N. Oakhurst Dr., P4, Beverly Hills, Calif. 90210

[21] Appl. No.: 666,891

[22] Filed: Mar. 8, 1991

[51] Int. Cl.⁵ .......................................... B65D 85/48
[52] U.S. Cl. .............................. 206/456; 206/45.31; 206/454; 206/453
[58] Field of Search ............... 206/456, 45.31, 586, 206/521, 454, 453, 455, 449, 450

[56] References Cited

U.S. PATENT DOCUMENTS

| | | | |
|---|---|---|---|
| 1,274,804 | 5/1917 | Spitzer | 206/456 X |
| 2,197,859 | 4/1940 | Freed | 206/456 |
| 3,643,650 | 2/1972 | Elder | 206/596 X |
| 3,710,975 | 1/1973 | Jansen | 206/456 |
| 3,746,161 | 7/1973 | Jones | 206/456 |
| 4,077,515 | 3/1978 | Shoberg | 206/456 |
| 4,589,551 | 5/1986 | Hellon | 206/456 |
| 4,819,804 | 4/1989 | Levy | 206/456 |
| 5,016,752 | 5/1991 | Haugen, Jr. | 206/455 |
| 5,044,500 | 9/1991 | Webber et al. | 206/456 |
| 5,045,173 | 9/1991 | Guadagno et al. | 206/456 X |
| 5,090,568 | 2/1992 | Tse | 206/456 |

FOREIGN PATENT DOCUMENTS 0284458 9/1988 European Pat. Off. ............ 206/521

Primary Examiner—Paul T. Sewell
Assistant Examiner—Ted Kavanaugh
Attorney, Agent, or Firm—Beehler & Pavitt

[57] ABSTRACT

A holder for packaging a biological specimen slide is heat formed from a single sheet of plastic. The holder has tray and cover portions separated by a hinge line, and when folded along the hinge line the cover closes a slide receiving recess on the tray portion. Integrally molded spacer elements positvely hold the slide to avoid smearing of the specimen. A window opening in the cover portion allows viewing of identification markings on one portion of the slide. An internal partition on the cover portion isolates the specimen bearing portion of the slide from exposure to the exterior environment through the window.

8 Claims, 2 Drawing Sheets

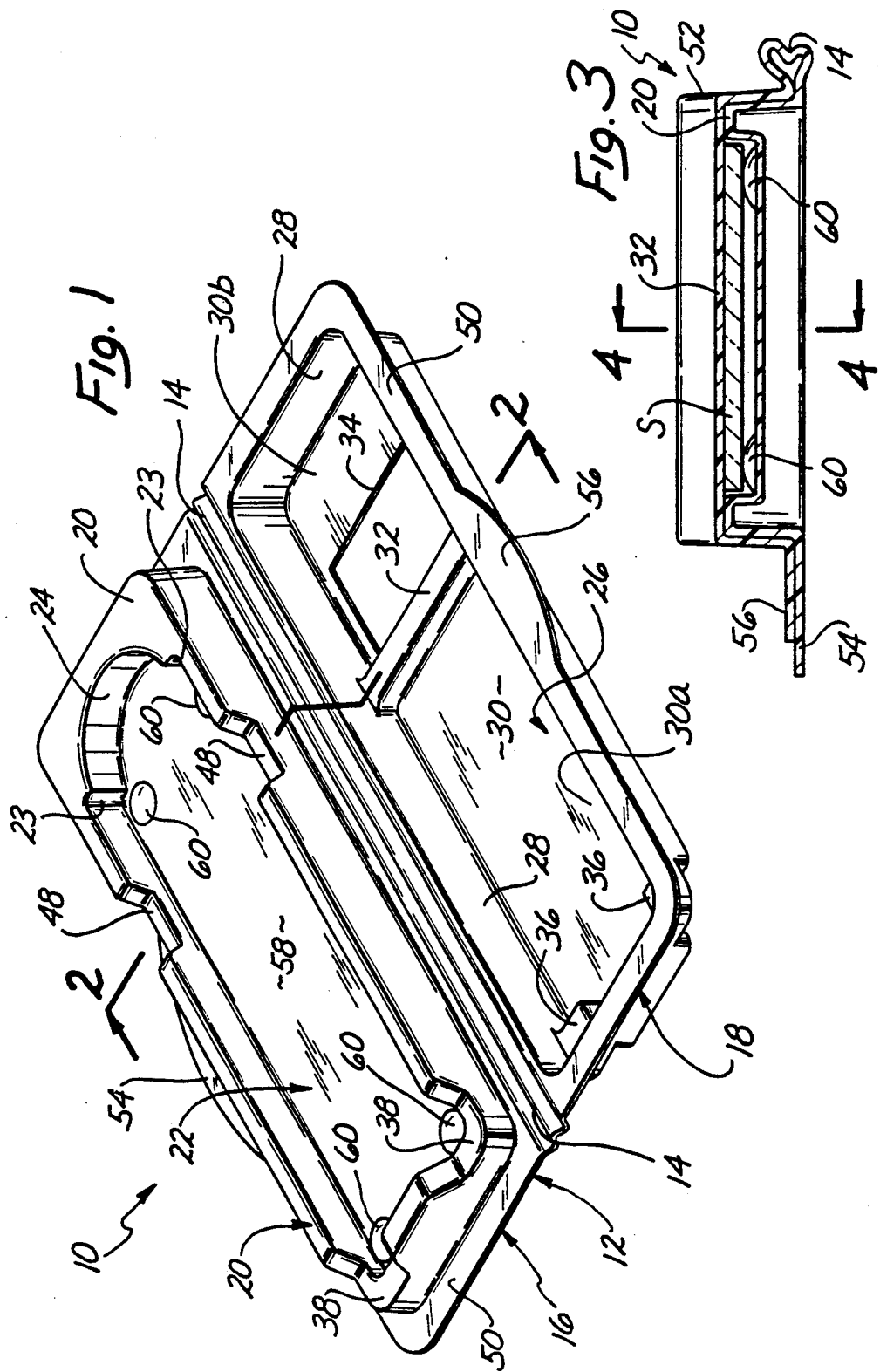

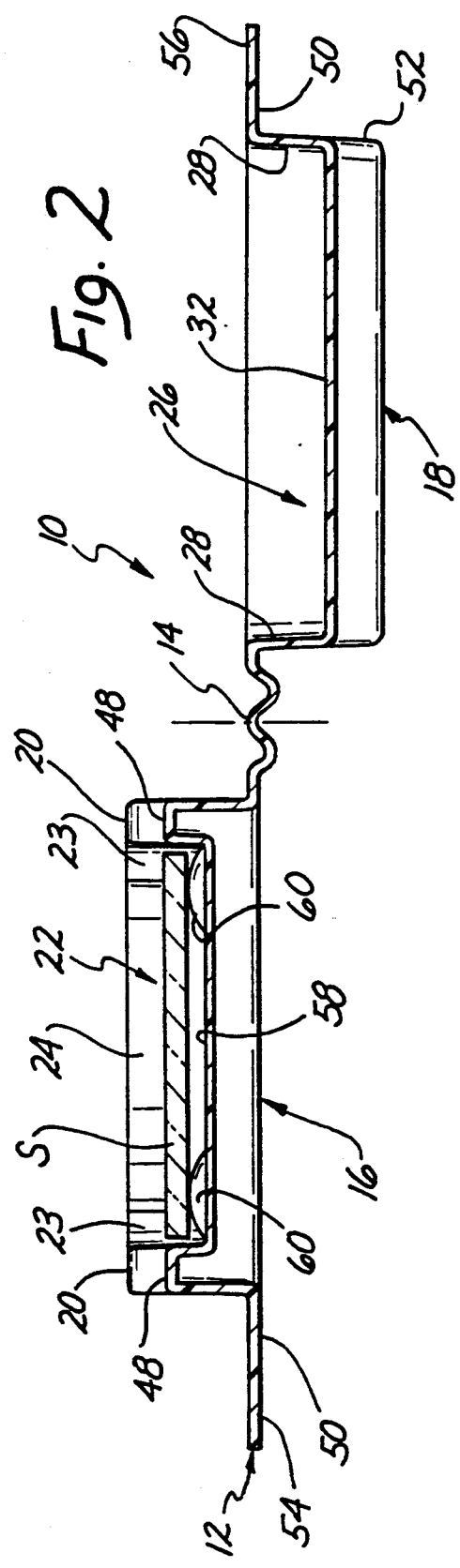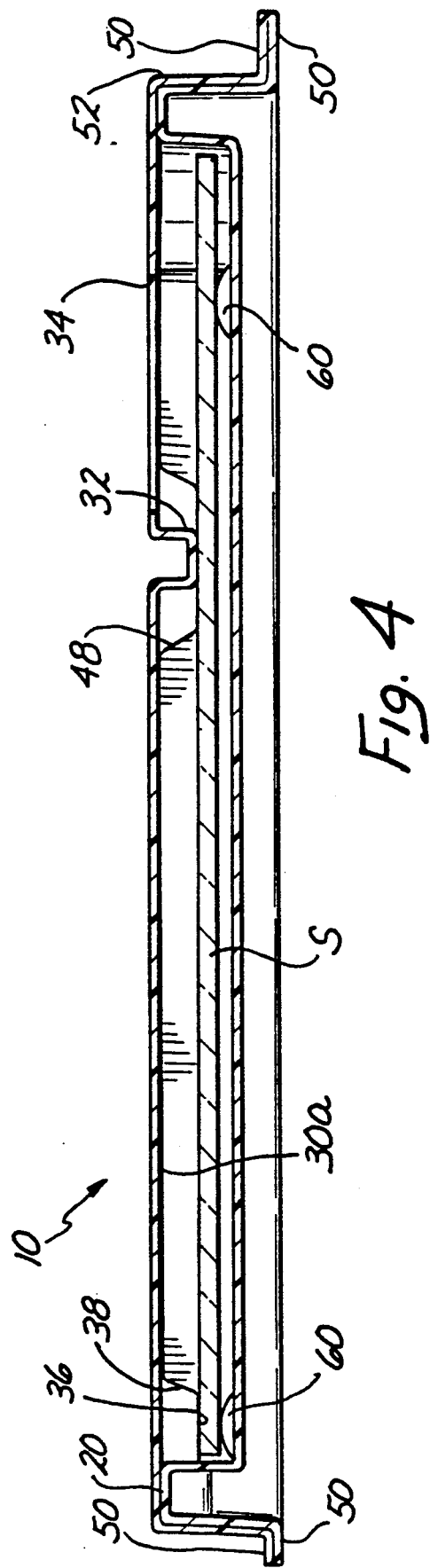

HOLDER FOR MEDICAL SPECIMEN SLIDE

FIELD OF THE INVENTION

The present invention relates to the field of medical disposables, and in particular to holders for slides used for conveying samples of biological tissues or fluids for laboratory analysis. The use of slides for this purpose is widespread not only in the medical and biological fields, but also in chemical and related analytical and experimental problems.

BACKGROUND OF THE INVENTION

The use of specimen slides, typically consisting of thin rectangular sheets of glass, for the collection, packaging and storage of biological specimens has prompted the design and fabrication of small, inexpensive, disposable packets and holders of various types, designs and materials. These items are intended to protect the relatively fragile glass slide and to preserve the specimen smeared or deposited on the slide against contamination or physical damage. Such packaging allows the specimen slide to be handled, stored and transported in a convenient and dependable manner until the specimen is processed, in the laboratory or otherwise.

U.S. Pat. No. 4,819,804, issued to this applicant, discloses a slide holder which includes a tray piece and a cover sheet molded of a light-weight yieldable material in the nature of Styrofoam. The tray piece defines a recess dimensioned to closely hold the edges of the specimen slide. Once the slide is pressed into the recess, it is retained therein by the lateral pressure exerted against the slide edges by the resilient material defining the side edges of the tray recess. This holds the slide securely at all stages of handling, including occasions when the holder is inverted with the slide faced down. The cover sheet is retained over the slide between raised edges integral with the tray piece.

While the holder disclosed in my earlier patent works well, further improvement is possible in order to facilitate and expedite the handling of both the slide and the package by all personnel involved in the specimen collection and specimen analysis procedures, while at the same time enhancing the level of protection afforded to both the specimen and the slide.

SUMMARY OF THE INVENTION

According to this invention a holder for a specimen slide of has a tray portion and a cover portion, a ridge defining a slide receiving recess in the tray portion, the cover portion being configured and dimensioned to make a friction fit with the ridge in a closed condition of the holder, and has a window in at least one of the portions for exposing to view an identification bearing portion of the slide in the closed condition of the slide holder. The window allows easy reading of the identifying indicia or markings typically written at one end of the slide by the person taking the sample to reference the biological sample to a particular patient or source. It therefore becomes unnecessary to open the holder package in order to view these identifying markings, which expedites the physical handling of the package and reduces the possibility of damage, contamination or loss of the slide and specimen.

Preferably, a partition is provided on the windowed portion or portions, the partition being adapted to bear against the slide and close off a specimen bearing portion of the slide from exposure to the window means thereby to avoid possible contamination of or physical damage to the specimen. This partition can be formed integrally with the holder.

It is also preferred to provide a number of spacer elements on both the tray and cover portions for supporting the slide in spaced relationship and away from contact with interior surfaces of both said tray and cover portions, particularly the bottom surface of the tray recess and the interior surface of the cover overlying the specimen bearing portion of the slide. This spacing prevents smearing of the biological specimen onto the interior of the holder.

The spacer elements may include a number of small raised bumps in the recess, opposed by the aforementioned partition and other raised elements on the cover portion, cooperating such that a slide is securely held therebetween The various spacer elements, excepting the partition, are best arranged so as to contact marginal areas of the slide surrounding the specimen bearing portion of the slide, so as to avoid contact between the specimen and any portion of the holder.

The entire slide holder may be molded of a single sheet of thermoplastic material for low cost large volume production and for ease of use and handling.

In alternate forms of this invention, the window may be omitted in a one-piece molded slide holder with or without the integral slide spacer elements as described above. Such a configuration might be attractive, for example, if the article is molded from clear plastic. Also, more than one window opening may be provided, for example, one window in each of the tray and cover portions to allow viewing of both sides of the slide by turning over the package without opening or handling the slide. In the latter embodiment, each of the tray and cover portions may be provided with a partition for isolating the specimen bearing area of the slide from exposure to either window.

These and other features and advantages of the present invention will be better understood by reference to the following detailed description of the preferred embodiments and the attached drawings.

BRIEF DESCRIPTION OF THE DRAWINGS

FIG. 1 is a perspective view of a specimen slide holder according to a first embodiment of this invention;

FIG. 2 is a cross section taken along line 2—2 in FIG. 1;

FIG. 3 is a cross section as in FIG. 2 but with the holder in closed condition;

FIG. 4 is a longitudinal section of the closed holder taken along line 4—4 in FIG. 3;

DETAILED DESCRIPTION OF THE PREFERRED EMBODIMENTS

With reference to the attached drawings, FIG. 1 shows a medical specimen slide holder 10 according to this invention. All features of the slide holder 10 shown in the drawings and described below can be formed on a base sheet 12 as an integral unit in a single heat forming and die cutting step from thin thermoplastic sheet material. The base sheet 12 is divided by a hinge line 14 into a tray portion 16 and cover portion 18. A peripheral flange 50 encompasses both the tray portion 16 and cover portion 18 and defines the plane of the base sheet 12 from which the three dimensional features described above are molded. This is best understood by reference to FIG. 2, which shows the three dimensional forming of the originally planar base sheet 12, and in particular illustrates the deformation of the base sheet plane in mutually opposite directions.

A ridge 20 on the tray portion 16 defines a generally rectangular tray recess 22 which is shaped and dimensioned to receive a specimen slide S as shown in FIGS. 2 through 4. One end of the tray recess is defined by end surfaces 23, and an arcuate cove 24 between the end surfaces 23 allows a fingertip to engage the edge of the slide S in order to lift the slide out of the tray recess.

The ridge 20 rises on the base sheet 12 as a male structure one side of the hinge line 14, while the cover portion 18 is molded to form female shell 52 projecting downwardly from the base sheet on the opposite side of the hinge line 14. The shell 52 fits closely about and makes retentive frictional engagement with the ridge 20 to hold tray portion 16 and cover portion 18 in the closed condition of FIGS. 3 and 4, and also to provide a substantial seal of the interior of the closed holder 10.

The concave side of the shell forms a rectangular cavity 26, with a side wall 28 and an internal surface or bottom 30 which forms the cover top and overlies the slide in the tray recess 22. The interior of the shell cavity 26 is divided into sections 30a and 30b by a ridge partition 32 which rises from the inner surface 30 to a height somewhat greater than one third the height of the side wall 28, and extends the full width of the cavity transversely to the hinge line 14. A rectangular window opening 34 is cut into the section 30b of the cover bottom 30, adjacent to the partition 32. The cover portion 18 also features two corner blocks 36 which rise to the same height as the partition 32 in the cover shell cavity 26.

The ridge 20 of the tray portion 16 has a pair of corner notches 38 and two side notches 40 which respectively admit the corner blocks 38 and the partition 32 of the cover portion 18, when the holder 10 is folded along the hinge line 14 to a closed condition illustrated in FIG. 3 and 4.

FIG. 2 shows that the ridge 20 is hollow on its underside and is created by deformation of the base sheet in a suitable forming die. This forming die preferably also performs a cutting operation to make the window opening 34, trim the edge and corners of the flange 50, and to form a pair of tabs 54 and 56 which extend from opposite free edges of the holder 10 as shown in FIGS. 1 and 2. When the holder 10 is folded to the closed condition of FIG. 3, the two tabs are joined in overlying relationship, with the lower tab 54 projecting somewhat beyond the edge of the upper tab 56. This facilitates manual separation of the two tabs which can then be pulled apart to open the package 10 for access to its interior.

FIGS. 2 through 4 show a typical medical specimen slide S placed in the tray recess 22 of the slide holder 10. Four slide spacer elements 60 in the form of small rounded bumps rise from the tray bottom 58 and support slide S away from contact with the tray bottom. The spacer elements 60 are positioned so as to contact marginal areas of the slide, in this case near the four corners of the slide, to avoid contact with more central, specimen bearing portions of the slide. In the closed condition of the holder 10 the corner blocks 36 extend into the tray recess 22 opposite the spacer elements 60 adjacent the corner notches 38. The height of the spacer elements 60 on the tray portion, and the partition 32 and corner blocks 36 on the cover portion 18 are such as to hold the slide S substantially clamped therebetween as shown in FIGS. 3 and 4, in spaced relationship and away from contact with both the tray bottom 58 and the cover bottom 30, to avoid smearing of the specimen against the interior surfaces of the holder package 10.

As best seen in FIGS. 3 and 4, in the closed condition of the holder package 10, the partition 32 makes contact with and bears against the slide S, and effectively partitions the interior of the holder into two chambers, one containing the specimen bearing portion of the slide S to the left of partition 32 in FIG. 4, the other containing the indicia bearing portion of the slide S on the right hand side of the partition 32. The partition 32 thus isolates and protects a biological specimen on the slide S against exposure to outside environment through the window opening 34. This prevents entry of dust, humidity or other contaminants into the specimen containing portion of the closed package, and generally minimizes the exposure of the specimen to the exterior atmosphere and the environment. The cover 18 makes a substantially tight seal along the entire rectangular perimeter of the ridge 20 to further close off entry of the exterior atmosphere the closed holder 10. This cover seal together with the sealing engagement of the partition 32 with the slide S affords a significant degree of protection to the specimen against damage or contamination through exposure to the exterior environment, while offering the convenience of the window opening 34 for easy and safe inspection of identifying markings or indicia on the slide S.

While a particular embodiment of the invention has been shown and illustrated for purposes of clarity and example, it must be understood that many changes, substitutions and modifications to the described embodiment will be apparent to those possessed of ordinary skill in the art without departing from the scope and spirit of the present invention which is defined by the attached claims. In particular, more than one window opening 34 may be provided on one or both of the tray and cover portions of the holder 10 and such windows may be provided with a plurality of ridge partitions 32 for isolating portions of the specimen slide against exposure to the outer environment. In yet another form of the invention, the holder 10 may be devoid of any window opening 34 while retaining some or all of the various internal slide spacer elements, such as bumps 60, corner blocks 36 and partition 32, for supporting a specimen bearing slide away from contact with the interior surfaces 58, 30 of the holder 10 to prevent smearing of a specimen. In still another form of the invention, the interior slide spacer elements may also be eliminated, to provide a basic one piece slide holder molded in three dimensional form from a single base sheet of thermoplastic material with a tray portion 16 and cover portion 18 divided by a hinge line 14. In still other forms of the inventions, the holder 10 of FIG. 1 may be manufactured as two pieces separated along the hinge line 14 of FIG. 1. This alternate embodiment may or may not include one or more window openings 34 and slide spacer elements 60, 36 and 32 as described above.

What is claimed is:

1. A unitary holder for a medical specimen slide formed from a single originally planar thin sheet of moldable material into a three dimensional structure wherein said sheet retains a substantially uniform thickness throughout said holder, said sheet divided along a hinge line into a tray portion and a cover portion and having a peripheral flange defining a base plane in an open condition of said holder:

a male ridge structure rising above said plane on said tray portion, said ridge structure defining a tray recess including a tray bottom dimensioned to receive the specimen slide;

a concave shell formed below said plane in said cover portion, said shell defining a cavity including a cover top and a side wall adapted to mate onto said ridge structure in a folded condition of said holder for covering said slide; and spacer means integral with said sheet for supporting said slide in spaced relationship away from contact with said tray bottom and said cover top.

2. The holder of claim 1 wherein said spacer means comprise small bumps integral with said tray bottom and positioned to contact marginal areas of the slide.

3. The holder of claim 1 wherein said cover portion is retained in said closed condition by a friction fit with said ridge means.

4. The holder of claim 1 wherein said spacer means comprise a partition extending between opposite side walls across said cover top in said cavity, and side notches in said ridge structure for receiving said partition in a closed condition of said holder, said partition dividing said cavity into a first portion and a second portion, said partition cooperating with spacer elements on said tray bottom for holding said slide said spaced relationship.

5. The holder of claim 1 wherein said spacer means include corner block elements formed to two corners of said cavity and corner notches in said ridge structure configured to receive said corner block elements in a closed condition of said holder, said corner block elements opposing spacer elements on said tray bottom for holding said slide therebetween in said spaced relationship.

6. The holder of claim 4 further comprising a window opening cut in said cover top in said second portion, said window opening overlying a substantial portion of a top surface of the slide, said partition protecting a remaining portion of said slide from exposure to said window opening.

7. The holder of claim 1 wherein said peripheral flange includes tab means on opposite edges of said sheet to provide a finger hold and facilitate manual separation of said cover and tray portions when opening said holder.

8. A unitary holder for a medical specimen slide formed from a single originally planar thin sheet of moldable material into a three dimensional structure wherein said sheet retains a substantially uniform thickness throughout said holder, said sheet divided along a hinge line into a tray portion and a cover portion and having a peripheral flange defining a base plane in an open condition of said holder;

a male ridge structure rising above said plane on said tray portion, said ridge structure defining a tray recess including a tray bottom dimensioned to receive the specimen slide;

a concave shell formed below said plane in said cover portion, said shell defining a cavity including a cover top and a side wall adapted to mate onto said ridge structure in a folded condition of said holder for covering said slide;

a partition extending between opposite side walls across said cover top in said cavity and corner block elements formed at two corners of said cavity, and notches in said ridge structure for receiving said partition and corner blocks in a closed condition of said holder, said partition dividing said cavity into a first portion and a second portion, said partition and corner blocks cooperating with spacer elements on said tray bottom for holding said slide in said spaced relationship away from contact with said tray bottom and said cover top; and a window opening cut in said cover top in said second portion, said window opening overlying a substantial portion of a top surface of the slide, said partition protecting a remaining portion of said slide from exposure to said window opening.

* * * * *